United States Patent [19]

Millard

[11] Patent Number: 4,505,902

[45] Date of Patent: Mar. 19, 1985

[54] SKIN TREATMENT PREPARATION

[76] Inventor: Mary A. Millard, 2068 Belover Dr., Memphis, Tenn. 38127

[21] Appl. No.: 582,078

[22] Filed: Feb. 21, 1984

Related U.S. Application Data

[63] Continuation-in-part of Ser. No. 418,592, Sep. 15, 1982, abandoned.

[51] Int. Cl.³ .............................................. A61K 35/78
[52] U.S. Cl. ................................................. 424/195.1
[58] Field of Search .............................. 424/195, 107; 260/236.6

[56] References Cited

U.S. PATENT DOCUMENTS 4,201,235 5/1980 Cravatta ................................ 424/47

OTHER PUBLICATIONS

Merck Index #1531, BHA, p. 197, 1976, 9th ed.

Primary Examiner—Albert T. Meyers
Assistant Examiner—John W. Rollins, Jr.
Attorney, Agent, or Firm—Kalish & Gilster

[57] ABSTRACT

A preparation for treatment of the skin to provide moisture thereto, to promote healing, to maintain a healthy condition; as well as to concurrently produce a pleasing cosmetic effect. The preparation comprises refined mineral oil, apricot kernel oil, avocado oil, aloe vera juice, together with vitamins provided by cod liver oil and preservatives.

3 Claims, No Drawings

SKIN TREATMENT PREPARATION

This is a continuation-in-part of application Ser. No. 418,592 filed Sept. 15, 1982, now abandoned, for Skin Treatment Preparation.

BACKGROUND AND SUMMARY OF THE INVENTION

This invention relates in general to skin treatment compositions for promoting and maintaining the skin in a healthy state, such as, by providing adequate moisture, effecting healing, and assuring of requisite nutrients.

Heretofore, various compositions have been developed for the purpose of treating human skin for conducing to the healthy state thereof, as well as for concomitant cosmetic purposes. Thus, many such preparations have been of a moisturizing character to protect the skin against drying which is causative of wrinkling, as may be occasioned by subjection to solar radiation, as well as to the normal aging process; while other preparations have been intended to present a cosmetic effect together with promotion of lubrication, obscuring of blemishes and the like. However, invariably such current formulations have been relatively complex, being comprised of a considerable number of ingredients, many of which are exotic and the compounding of such formulations has proved to be a relatively involved, time-consuming procedure, necessitating developed skills on the part of the compounder.

Exemplary of the inadequacies of the prior art is the lubricating and cosmetic preparation set forth in U.S. Pat. No. 3,818,105 which incorporates isoparaffinic hydrocarbon fractions, having between 12 and 14 carbon atoms as the basic ingredient and with such being admixed with various other components, such as, water, alcohols, humectants, clay minerals, and inorganic silicates, as well as dyes, surfactants, perfumes, and the like.

The use of oat flour in skin moisturing creams and lotions is disclosed in U.S. Pat. No. 4,014,995, the same being the primary constituent in view of its stated property of oil and water adsorption. The oat flour is compounded with numerous other ingredients by way of a multi-step intricate compounding procedure. U.S. Pat. No. 3,133,864 teaches the provision of a skin conditioner wherein the basic component is relatively exotic, being at least one bitter component of the plant Swertia Japonica Makino. According to the patentee therein such plant and analogous plants possess properties for improving the condition of the skin. Expectedly, the method of preparing such compositions is time consuming, very intricate, and necessitates the services of a skilled artisan.

U.S. Pat. No. 3,957,971 is also exemplary of the deficiencies of the prior art, that is, presenting skin treatment agents of a highly complicated formulation. Therein is disclosed compositions comprising liposomes which constitute a matrix of a lipid mixture having cavities therein for containing a humectant in aqueous solution for retarding water loss by the skin and, thus, statedly inhibiting the development of dry, rough, chapped, and scaly skin.

Therefore, it is an object of the present invention to provide a skin treatment composition which is comprised of ingredients well known to the average individual and which are readily available, as distinguished from exotic, complex or costly agents which have constituted the primary ingredient of skin treatment compositions heretofore known.

It is another object of the present invention to provide a skin treatment formulation which may be readily compounded without the necessity of developed skill on the part of the compounder and with the compounding technique not requiring any involved expensive equipment, nor necessitating the exercise of close maintenance of environmental conditions since compounding may be effected under ambient conditions.

It is a still further object of the present invention to present a skin treatment preparation which has demonstrated excellent properties of promoting the health of the skin by providing moisture thereto, as well as maintaining said moisture within the membranes and in addition possesses excellent healing properties, together with supplying vital nutrients.

It is another object of the present invention to provide a skin treatment composition which by virtue of its skin health promoting characteristics, also has a marked cosmetic effect so that the skin will present a soft, pleasing, fresh appearance.

It is a still further object of the present invention to provide a skin treatment preparation which may be most economically produced; which is comprised of natural ingredients, as distinguished from synthesized agents; which has extensive shelf life; wherein limited quantities are productive of beneficial results so that it is economical in usage; which is pleasing in appearance and without potential harm to the user.

DESCRIPTION OF THE INVENTION

The present invention constitutes a skin treatment preparation or agent which is comprised of natural ingredients, being intermixed and compounded in such relative proportionalities as to bring about a resultant effect which exceeds such as would be expected from merely adding the individual ingredients together. Thus, the combination of components of the present preparation brings about a certain synergism whereby the treated skin is subjected to a moisturizing effect, a marked healing benefit, as well as a cosmetic result, which far exceeds that which would normally be expected by a mere intermixture of the constituents.

The essential elements of this preparation are refined mineral oil, apricot kernel oil, avocado oil, and aloe vera juice. Refined mineral oil, which is the major ingredient of this present preparation, is naturally occurring in that it is obtained from crude petroleum, as by fractionation, and is peculiarly adapted to provide lubrication to the skin by reason of its inherent constituents and possess a desired skin-penetrating ability; that is, penetration of the epidermis, but which will not penetrate for absorption into the blood stream. Mineral oil, being a refined pure oil, is thus devoid of agents which might in some way be harmful to the skin and may be most economically obtained. Avocado oil is also a natural oil and has the capacity of both providing moisture, as well as promoting the retention of the same within the skin so that it resists loss of moisture through drying, as upon exposure to the sun or through the normal aging process wherein the membranes tend to in some way lose the capacity to retain moisture. This oil is obtainable from the pulp of the avocado and is, thus, indeed a natural product. Similarly, apricot kernel oil, which is also a pure oil produced from the fruit, has numerous properties beneficial to the skin. In addition to providing moisture, it possesses a healing capacity and, thus, is protective of the skin, as well as being readily absorbed therein. Apricot kernel oil also will endow the treated skin with a soft texture and, thus, provide a very attractive appearance. The therapeutic or healing effect obtained by use of the present preparation is markedly enhanced by the inclusion of the extract or juice from aloe vera which is a species (Curacao Aloe) of the aloe genus, and is, thus, the inspissated juice of the leaves of such plant. Accordingly, the juice or extract of aloe vera contains the known healing properties of such plant and provides nutrients to the skin for promoting the health thereof.

In addition to the aforementioned primary ingredients, the present preparation includes wheat germ oil and cod liver oil essentially for their inherent vitamin content, as well as certain preservatives, such as, propylparaben and TENOX BHA*. These ingredients are in relatively small amounts. Recognizedly, cod liver oil provides vitamins A and D, while wheat germ oil, which is another naturally occurring ingredient, being derived from the germ of wheat, is rich in natural vitamin E; such being otherwise generally referred to as d-alpha tocopherol. The wheat germ oil through its inherent properties has a healing effect upon the skin and will provide a pleasing glow and a certain shininess reflective of the healty condition produced by the present invention. The vitamins present in cod liver oil expectedly present beneficial nutrients so that such oil serves as a skin tonic. Propylparaben is incorporated for its preservative properties; while TENOX BHA is embodied within the preparation for its antioxidant capability which inhibits rancidity. The propylparaben and TENOX BHA prevent deterioration of the present invention so as to assure of a substantially indefinite shelf life.

*The term TENOX BHA is a trademark of Eastman Chemical Products, Inc. for food grade antioxidants. BHA is an abbreviation for butylated hydroxyanisole (The Condensed Chemical Dictionary, 9th Edition, Van Nostrand Reinhold Company, 1977).

The aforesaid ingredients are related in a carefully controlled relationship, with the precise proportionalities causing the unusual effects of the present invention which markedly distinguishes same from skin treatment preparations designed for the same general purpose heretofore known.

The following amounts and proportions are as follows:

| INGREDIENT | PERCENTAGE BY WEIGHT |
| --- | --- |
| Refined Mineral Oil | 54.25% |
| Apricot Kernel Oil | 26.00% |
| Aloe Vera Juice | 18.00% |
| Wheat Germ Oil | 1.00% |
| Avocado Oil | 0.50% |
| Cod Liver Oil | 0.10% |
| Propylparaben | 0.10% |
| TENOX BHA | 0.05% |

Utilizing the above general formula, if one were to compound said preparation to produce 500 grams thereof, the following would constitute the relative amounts involved:

| INGREDIENT | PERCENTAGE BY WEIGHT |
| --- | --- |
| Refined Mineral Oil | 272.00 gr. |
| Apricot Kernel Oil | 130.00 gr. |
| Aloe Vera Juice | 89.25 gr. |
| Wheat Germ Oil | 5.00 gr. |
| Avocado Oil | 2.50 gr. |
| Cod Liver Oil | 0.50 gr. |
| Propylparaben | 0.50 gr. |
| TENOX BHA | 0.25 gr. |

The compounding of the present invention may be achieved very economically and rapidly. The refined mineral oil, apricot kernel oil, avocado oil, and aloe vera juice are intermixed by suitable agitation, as by a standard agitator. A very small quantity, approximately 1%, of such intermixture is then added to the other ingredients, namely wheat germ oil, cod liver oil, propylparaben, and TENOX BHA for the purpose of dissolving the same within the aforesaid small amount of the intermixture of mineral oil, apricot kernel oil, avocado oil, and aloe vera juice. The solution formation may be accelerated by subjecting the said limited amount of the aforesaid intermixture and the said remaining ingredients to heat, within the range of approximately 50° C. to 60° C., with attendant agitation. Understandably, without the heat, the solution formation may be effected under ambient conditions with agitation. The resultant solution is then poured into the balance of the aforesaid intermixture with agitation being effected until the preparation ingredients present a homogeneous appearance possessing a generally yellow, or olive-greenish, color.

As stated above, the present invention provides the skin with moisture, as well as a healing effect, in addition to also presenting a protective capacity. The oils are highly absorptive within the epidermis and, thus, thereby carry moisture and lubrication to the skin membranes, as well as promoting penetration of the entrained vitamins, without danger of blood stream absorption.

Thus, a skin treatment preparation incorporating the present invention may be most economically produced, there being no necessity for complex, costly equipment, nor for concern as to the conditions under which the compounding is effected since ambient conditions are satisfactory. Furthermore, individuals producing the present invention do not require any developed skills, but may effect production in a most readily and reliable manner upon initial instruction.

From the foregoing, the utilization of the present invention should be obvious since the same is merely applied directly to the individual's skin in small amounts, which are then lightly rubbed or massaged into the skin surface being treated. The preparation is readily absorbed so that the initial oiliness dissipates and a fresh, glowing appearance is promptly achieved.

I claim:

1. A skin treatment preparation having the following formulation:

| INGREDIENT | PERCENTAGE BY WEIGHT |
| --- | --- |
| Refined Mineral Oil | 54.25% |
| Apricot Kernel Oil | 26.00% |
| Aloe Vera Juice | 18.00% |
| Wheat Germ Oil | 1.00% |
| Avocado Oil | 0.50% |
| Cod Liver Oil | 0.10% |
| Propylparaben | 0.10% |
| Butylated Hydroxyanisole | 0.05% |

2. A skin treatment preparation according to claim 1 wherein the same is prepared by intermixing the refined mineral oil, apricot kernel oil, avocado oil, and aloe vera juice under agitation, a quantity of approximately 1% by volume of the said intermixture is then added to a mixture of the wheat germ oil, cod liver oil, propylparaben, and butylated hydroxyanisole, the said mixture together with the approximately 1% of the aforesaid intermixture is subjected to agitation until said wheat germ oil, cod liver oil, propylparaben, and butylated hydroxyanisole are dissolved in the received quantity of intermixture of the oils and aloe vera juice, and then such solution is poured into the balance of the intermixture of the refined mineral oil, apricot kernel oil, avocado oil and aloe vera juice and the ingredients are then agitated until the resultant preparation presents a generally yellow, or olive-greenish, coloration, said method being conducted under ambient conditions.

3. A skin treatment preparation according to claim 2 wherein the mixture of the wheat germ oil, cod liver oil, propylparaben, and butylated hydroxyanisole is subjected to heat within the range of approximately 50° C.–60° C. with concurrent agitation during addition of the approximately 1% of the oil and aloe vera juice intermixture for accelerating solution formation.

* * * * *